United States Patent [19]

Till

[11] Patent Number: 5,552,114

[45] Date of Patent: Sep. 3, 1996

[54] STERILIZATION OF KEGS

[75] Inventor: Volker Till, Hofheim am Taunus, Germany

[73] Assignee: GEA Till GmbH & Co., Kriftel, Germany

[21] Appl. No.: 404,966

[22] Filed: Mar. 16, 1995

[30] Foreign Application Priority Data

Mar. 16, 1994 [DE] Germany .......................... 44 08 839.6

[51] Int. Cl.$^6$ ..................................................... A61L 2/06
[52] U.S. Cl. .................................. 422/26; 422/1
[58] Field of Search ................... 422/1, 26, 119

[56] References Cited

U.S. PATENT DOCUMENTS 4,573,505  3/1986  Lee et al. ................................. 141/92
5,285,825  2/1994  Townsley ................................. 141/9

FOREIGN PATENT DOCUMENTS

3502242A1  1/1985  Germany .
4010921C2  4/1990  Germany .

Primary Examiner—Robert J. Warden
Assistant Examiner—Theresa T. Snider
Attorney, Agent, or Firm—Chilton, Alix & Van Kirk

[57] ABSTRACT

The sterilization of reusable kegs in which a consumable beverage is dispensed includes pressurization of the keg with steam, measuring the residual pressure after a time delay which may vary, and comparing the residual pressure against a standard pressure read from a cooling curve which plots pressure decay vs. time delay. A family of standard cooling curves will be stored for each type keg to be sterilized with the curves for each keg being a function of the difference between the steam and ambient temperatures.

14 Claims, 1 Drawing Sheet

STERILIZATION OF KEGS

BACKGROUND OF THE INVENTION

1. Field of the Invention

The present invention relates to the sterilization of containers which are used in the beverage industry and particularly to improvements in techniques for ensuring that reusable barrels have been adequately cleaned and are free of leaks. More specifically, this invention is directed to improvements in and to a process wherein metal kegs are charged with a heated sterlilizing agent under pressure for the purpose of cleaning. Accordingly, the present invention is directed to novel and improved methods of such character.

2. Description of the Prior Art

In the beverage industry, it is common practice to employ reuseable containers, i.e., barrel like kegs, in the distribution chain between the brewer/bottler and the consumer. As is well known, such kegs have a screw-in fitting which includes an automatic shut-off valve. In order to ensure that the product in the keg will not degrade, a very high degree of container cleanliness must be achieved and maintained after each use. Thus, before being filled or refilled, the containers are sterilized, typically through the use of steam. The steam is introduced into the container under pressure and the container thereafter closed. The container, i.e., the keg, will be comprised of a metal such as stainless steel and the sterilization procedure will take place under ambient conditions. Accordingly, there will be a temperature differential across the keg wall and, accordingly, heat transfer through the wall of the keg. The internal temperature will fall as a result of this heat transfer and condensation of the steam will result. As the steam condenses, the pressure within the container will also fall. If the pressure within the keg falls below the ambient pressure, air will be sucked into the keg and sterility will be compromised. Thus, in the prior art, a pressure measurement is taken a predetermined time after the keg has been filled with steam and closed. The purpose of this pressure measurement is to exercise quality control over the sterilization process, and particularly to guarantee sterility, by determining whether there is a positive pressure in the keg after the waiting period.

In the conventional steam sterilization process as briefly described above, because of unrelated problems that may be encountered in the kegging plant, the waiting period varies from container to container, i.e., some kegs are kept under pressure longer than others. As the waiting period between steam pressure build-up and measuring the residual pressure increases, the pressure in the container steadily decreases because of the above-discussed temperature equalization with the surrounding air. It has been the previous practice in the art to simply determine whether or not the pressure within the keg is above the ambient atmospheric pressure. If the measured pressure is not positive, i.e., above ambient, the container is not filled. No more extensive analysis of the sterilization process is performed. There has, however, long been a need for providing more accurate information as to the quality of the sterilization process and the information desired should also be indicative of whether there are any leaks in the container.

SUMMARY OF THE INVENTION

The present invention overcomes the above-briefly discussed and other deficiencies and disadvantages of the prior art by providing a novel and improved sterilization technique wherein standard cooling curves, i.e., plots of pressure vs. time, are obtained for each of the different kegs a brewery, for example, will employ. These standard cooling curves will be stored, preferably in a computer. Thereafter, the time each container is closed after being pressurized and the time the residual pressure is measured are both recorded. The quality of the sterilization process is then determined by comparing the measured residual pressure with a pressure value corresponding to the actual waiting period, i.e., the time delay between pressurization and the residual pressure measurement, which is read from a standard cooling curve for the container being treated. The cooling curves will be plotted for "reference" containers known to be leak free and to have been properly sterilized.

The present invention contemplates the use of steam as the sterilization medium. The steam temperature will be selected, taking into account the expected waiting period, so that sufficient sterilization is guaranteed.

Assuming a constant ambient temperature, the rate of fall of pressure inside the container is directly dependent upon the temperature of the steam. In accordance with a preferred embodiment, a family of standard cooling curves will be plotted for various differences between steam temperature and ambient temperature. During the testing of a given keg, a standard cooling curve for that model keg plotted for approximately the same difference between steam temperature and ambient temperature will be employed.

As indicated above, each type of container employed for example, by a brewery will have its own standard cooling curves. The need for determining standard cooling curves for each type of container is dictated by the fact that differences in size, shape and wall thickness will influence heat transfer through the container wall and thus will influence the rate of fall of pressure in the container.

The present invention achieves fast and reliable analysis of the sterilization process by storing the standard cooling curves in a computer and employing the computer to evaluate the information collected during the sterilization process, i.e., the time of pressurization, the time the residual pressure is measured the magnitude of the residual pressure and the steam termperature.

A particularly useful and novel attribute of the present invention resides in the fact that, if the results of the analysis of the data collected for a particular keg show that its residual pressure after a particular time delay is outside of a fixed tolerance range on the appropriate standard cooling curve, the keg will be presumed to have a leak. Thus, if the analysis shows a residual pressure which is still positive but is below that which would be nominal on the appropriate standard cooling curve by more than a preselected amount, that container will not be refilled but rather will be subjected to further examination to determine whether there is in fact a leak.

BRIEF DESCRIPTION OF THE DRAWINGS

The present invention may be better understood, and its numerous objects and advantages will become apparent to those skilled in the art, by reference to the accompanying drawing wherein.

DESCRIPTION OF THE DISCLOSED EMBODIMENT

Figure 1A:
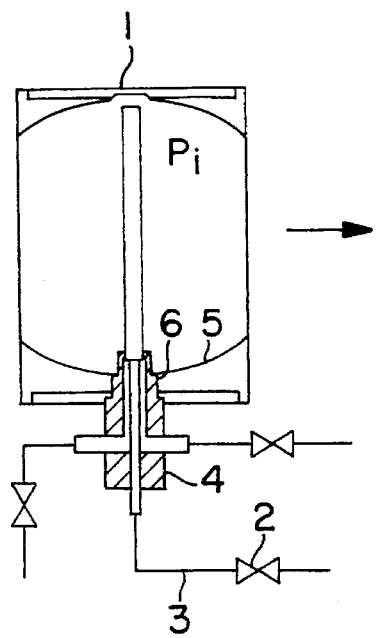
FIG. 1 schematically depicts three stages of a sterilization process in accordance with the invention.

Referring to FIG. 1A, a keg to be sterilized is indicated at 1. Keg 1 is provided with an integral fitting 6, screwed into the base 5 of the keg, which includes an automatic shut-off valve. In order to sterilize keg 1 prior to its being filled with a beverage, the keg is positioned on a processing head 4 and charged with steam. The steam is delivered via conduit 3 and admission thereof into keg 1 is controlled by means of valve 2. Valve 2 may, of course, automatically close when the desired initial keg pressure Pi is achieved.

The steam is injected into keg 1 until the internal pressure reaches level Pi. Typically, the steam source provides the steam at an excess pressure of two bar and the steam temperature will be selected as a function of the material from which keg 1 is fabricated and the usual sterilization time for that type keg. Keg 1 will usually be fabricated from stainless steel and, in a typical example where the sterilization time is approximately thirty seconds, the steam temperature would be 127° C.

Figure 1B:
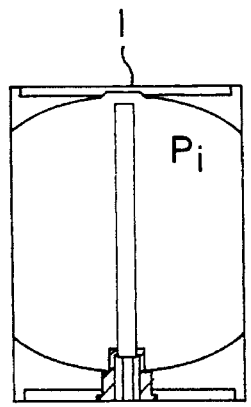

After keg 1 has been pressurized and valve 2 closed, the keg will be removed from processing head 4 as shown in FIG. 1B. The keg will remain closed for a waiting period $t_H$. Because of temperature equalization with the ambient air, the pressure Pi in keg 1 will fall steadily and, after a waiting period $t_H$, a residual pressure value $P_{iR}$ will exist.

Figure 1C:
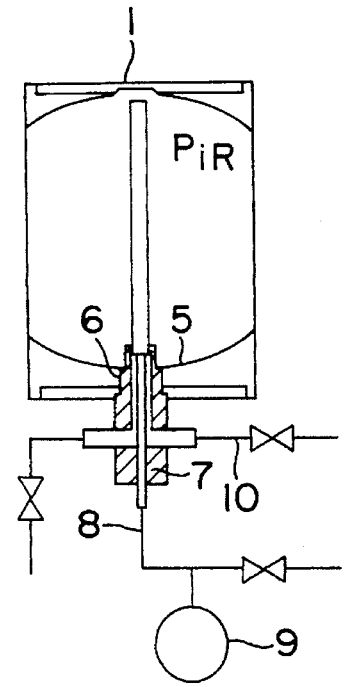

The waiting period $t_H$, as discussed above, will vary from keg to keg due to external factors. The keg will, after the waiting period, be mounted on a filling head 7 as shown in FIG. 1C. Upon mounting upon filling head 7, the residual pressure $P_{iR}$ is measured with a pressure measuring device 9. If the keg 1 receives a positive evaluation, as will be described in greater detail below, it will filled with the product liquid via a product feed conduit 10.

Figure 2:
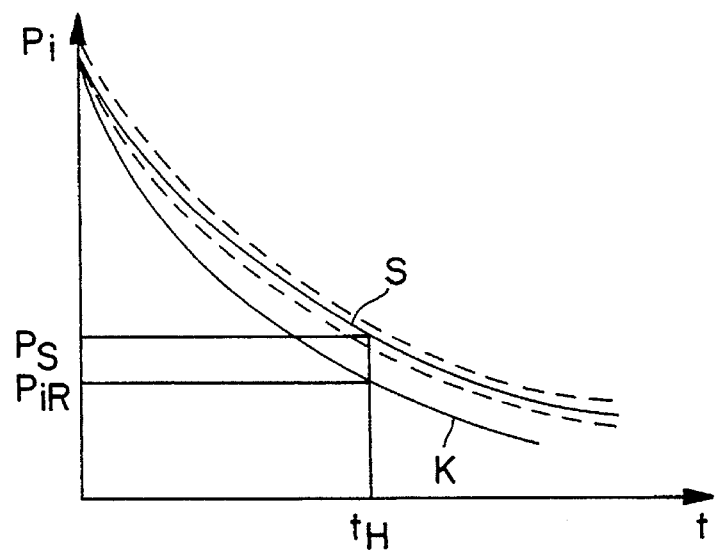
FIG. 2 is a pressure/time diagram depicting a standard cooling curve and a cooling curve for a defective barrel, FIG. 2 thus showing the analysis which is performed in accordance with the invention.

Referring to FIG. 2, a standard cooling curve for keg 1 may be experimentally determined by measuring, for a known $P_i$ and a known difference between the steam temperature and ambient temperature, the residual pressure $P_{iR}$ for various wait times $t_H$. This experimentally determined information can then be stored in a data storage device as a standard cooling curve. An example of such a standard cooling curve S is shown in FIG. 2, i.e., curve S is a pressure/time plot for a known or reference container. As may be seen from FIG. 2, the keg internal pressure decreases from the initial value $P_i$ as time increases. The cooling rate, and thus the slope of the standard cooling curve S, is a function of the rate of decrease of the temperature within keg 1.

In the monitoring of the sterilization process in accordance with the invention, the time the keg 1 was pressurized to level $P_i$ with steam will be recorded for each keg. Thereafter, when the keg is opened before filling, both the residual steam pressure $P_{iR}$ and the time of opening will be recorded. The actual steam pressure value measured, i.e., $P_{iR}$, will then be compared to a steam pressure value $P_S$ on curve S which corresponds to the duration of the waiting period $t_H$, i.e., the time between pressurization and residual pressure measurement. If the measured residual pressure level is outside of a preselected tolerance range, as represented by the two broken line curves to either side of the standard cooling curve S on FIG. 2, and particularly if the residual pressure $P_{iR}$ is below the tolerance range, it will be assumed that keg 1 has a hole or a damaged seal around fitting 6. Restated, if the measured residual pressure is still positive but below a value determined by reference to the standard cooling curve by more than a predetermined amount, it will be assumed that the pressure loss is in part due to a loss of volume to the ambient environment. Thus, the process of the present invention permits a check on both the sterilization process and the integrity of the keg. Referring again to FIG. 2, the cooling curve K represents a cooling curve representative of a keg which has a leak.

Since the pressure drop in keg 1 is directly dependent on the temperature difference between the admitted steam and the ambient air, the steam temperature when the keg is pressurized will be recorded. The standard cooling curve used to monitor the sterilization process will be the curve previously determined for that temperature. This curve selection is based upon the presumption that the ambient temperature in the bottling plant is substantially constant.

As also noted above, since the decrease in keg internal temperature, and thus also the pressure decay, is dependent on the type of container, a family of standard cooling curves will be plotted for each type of container.

The keg type information and the measured values of pressure, time and temperature are transferred to a data-processing device for selection of the appropriate cooling curve and comparison with the selected curve. This allows automatic processing of data and provides an efficient and reliable way to identify kegs which should be rejected and thus not refilled with beverage.

While a preferred embodiment has been shown and described, various modifications and substitutions may be made thereto without departing from the spirit and scope of the invention. Accordingy, the present invention has been described by way of illustration and not limitation.

What is claimed is:

1. In a process for the sterilization of containers by steam injection, the containers being of the type from which a pressurized liquid is dispensed, the process comprising the pressurization of a container to be sterilized at a time $t_1$ with steam at a pressure $P_i$, sealing the pressurized container and measuring the residual pressure $P_{iR}$ at a time $t_2$—at least commensurate with the achievement of the desired degree of sterilization, wherein $t_2$ is later than $t_1$, the improvement comprising the steps of:

recording the time $t_1$ when the container was sealed;

calculating the waiting time $t_H = t_2 - t_1$; and comparing the measured residual pressure $P_{iR}$ to a residual pressure $P_S$ from a standard cooling curve for the calculated waiting time to determine if the pressure $P_{iR}$ deviates from $P_S$ by more than a predetermined amount, any such deviation which is greater than the predetermined amount being evidence that the container has a leak.

2. The process of claim 1 wherein a family of standard cooling curves plotting $P_{iR}$ vs. $t_H$ are calculated for the container, standard cooling curves being determined for several differences between the steam temperature $t_1$ and the ambient temperature, and wherein the standard cooling curve corresponding to the existing temperature difference is used in the step of comparing.

3. The process of claim 2 wherein a plurality of types of container are to be sterilized and wherein said process further comprises:

preparing a standard cooling curve for each different type of container to be sterilized.

4. The process of claim 3 wherein the families of standard cooling curves are stored in a data processing device and the values of $t_1$, $t_2$ and $P_{1R}$ are inputted to the data processing device to perform the comparison.

5. The process of claim 2 wherein the standard cooling curves are stored in a data processor and the values of $t_1$, $t_2$ and $P_{iR}$ are inputted to the data processor to perform the comparison.

6. The process of claim 1 wherein a plurality of types of container are to be sterilized and wherein said process further comprises:

preparing a standard cooling curve for each different type of container to be sterilized.

7. The process of claim 6 wherein the standard cooling curves are stored in a data processor and the values of $t_1$, $t_2$ and $P_{iR}$ are inputted to the data processor to perform the comparison.

8. The process of claim 1 wherein the standard cooling curve is stored in a data processor and the values of $t_1$, $t_2$ and $P_{iR}$ are inputted to the data processor to perform the comparison.

9. The process of claim 8 wherein the steam temperature is also inputted into the data processor and the appropriate standard cooling curve is selected as a function of steam temperature.

10. The process of claim 1 further comprising:

establishing a tolerance range for residual pressures relative to the residual pressure P for each time delay; and rejecting a container if the measured $P_{iR}$ is outside of the tolerance range.

11. The process of claim 10 wherein a family of standard cooling curves plotting $P_{iR}$ vs. $t_H$ are calculated for the container, standard cooling curves being determined for several differences between the steam temperature $t_1$ and the ambient temperature, and wherein the standard cooling curve corresponding to the existing temperature difference is used in the step of comparing.

12. The process of claim 11 wherein a plurality of types of container are to be sterilized and wherein said process further comprises:

preparing a standard cooling curve for each different type of container to be sterilized.

13. The process of claim 12 wherein the standard cooling curve is stored in a data processor and the values of $t_1$, $t_2$ and $P_{iR}$ are inputted to the data processor to perform the comparison.

14. The process of claim 13 wherein the steam temperature is also inputted into the data processor and the appropriate standard cooling curve is selected as a function of steam temperature.

* * * * *

UNITED STATES PATENT AND TRADEMARK OFFICE
CERTIFICATE OF CORRECTION

PATENT NO. : 5,552,114
DATED : September 3, 1996
INVENTOR(S) : Volker TILL

It is certified that error appears in the above-indentified patent and that said Letters Patent is hereby corrected as shown below:

Column 4, line 37, after "$t_2$", delete "—".

Column 4, line 66, "$P_{1R}$" should read --$P_{iR}$--.

Column 5, line 24, "P" should read --$P_s$--.

Signed and Sealed this

Twenty-fifth Day of November, 1997

BRUCE LEHMAN

*Attest:*

*Attesting Officer*  *Commissioner of Patents and Trademarks*